(12) United States Patent
Labyed et al.

(10) Patent No.: US 11,717,256 B2
(45) Date of Patent: Aug. 8, 2023

(54) MOTION INDEPENDENCE IN ACOUSTIC RADIATION FORCE IMPULSE IMAGING

(71) Applicant: Siemens Medical Solutions USA, Inc., Malvern, PA (US)

(72) Inventors: Yassin Labyed, Maple Valley, WA (US); Liexiang Fan, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2004 days.

(21) Appl. No.: 14/991,635

(22) Filed: Jan. 8, 2016

(65) Prior Publication Data

US 2017/0196533 A1    Jul. 13, 2017

(51) Int. Cl.
*A61B 8/08* (2006.01)
*G01S 7/52* (2006.01)

(52) U.S. Cl.
CPC ................ *A61B 8/08* (2013.01); *A61B 8/485* (2013.01); *A61B 8/5276* (2013.01); *G01S 7/52022* (2013.01); *G01S 7/52042* (2013.01)

(58) Field of Classification Search
None
See application file for complete search history.

(56) References Cited

U.S. PATENT DOCUMENTS

| 8,532,430 | B2 | 9/2013 | Hazard |
| 8,727,995 | B2 | 5/2014 | Brunke |
| 9,794,394 | B2 | 10/2017 | Lee |
| 2008/0021319 | A1* | 1/2008 | Hamilton ............ G01S 7/52046 600/437 |
| 2008/0249408 | A1* | 10/2008 | Palmeri .................... A61B 8/08 600/438 |
| 2010/0160778 | A1* | 6/2010 | Eskandari .............. A61B 8/485 600/438 |
| 2012/0065507 | A1* | 3/2012 | Brunke ............... G01S 7/52042 600/442 |
| 2012/0089019 | A1 | 4/2012 | Fan |

(Continued)

FOREIGN PATENT DOCUMENTS

| CN | 104244838 A | 12/2014 |
| FR | 3031448 A1 | 1/2016 |
| JP | 2015-092937 | 5/2015 |

(Continued)

OTHER PUBLICATIONS

Sigrist et al. "Ultrasound Elastography: Review of Techniques and Clinical Applications", Theranostics 2017, vol. 7, Is. 5. pp. 1303-1329.*

(Continued)

*Primary Examiner* — Katherine L Fernandez
*Assistant Examiner* — Farouk A Bruce

(57) ABSTRACT

Motion independent acoustic radiation force impulse imaging is provided. Rather than rely on the displacement over time for each location, the displacements over locations for each time are used. Parallel beamforming is used to simultaneously sample across a region of interest. Since it may be assumed that the different locations are subjected to the same motion at the same time, finding a peak displacement over locations for each given time provides peak or profile information independent of the motion. The velocity or other viscoelastic parameter may be estimated from the displacements over locations.

19 Claims, 8 Drawing Sheets

(56) References Cited

U.S. PATENT DOCUMENTS

| | | | |
|---|---|---|---|
| 2012/0136250 A1* | 5/2012 | Tabaru | A61B 8/08 600/438 |
| 2012/0215101 A1* | 8/2012 | Maleke | A61B 8/08 600/438 |
| 2013/0024136 A1* | 1/2013 | Gallippi | G01N 29/343 702/41 |
| 2013/0218011 A1* | 8/2013 | Benson | A61B 8/485 600/438 |
| 2013/0267847 A1 | 10/2013 | Tamura | |
| 2014/0330122 A1* | 11/2014 | Baghani | A61B 8/485 600/438 |
| 2015/0005633 A1* | 1/2015 | Kanayama | A61B 8/5207 600/438 |
| 2015/0087976 A1 | 3/2015 | Fan | |
| 2015/0133783 A1 | 5/2015 | Tabaru | |
| 2015/0201905 A1 | 7/2015 | Ivancevich et al. | |
| 2016/0199034 A1 | 7/2016 | Labyed et al. | |

FOREIGN PATENT DOCUMENTS

| | | |
|---|---|---|
| KR | 2012-0035901 | 4/2015 |
| KR | 2015-0037689 | 4/2015 |

OTHER PUBLICATIONS

Dahl, et al., "A Parallel Tracking Method for Acoustic Radiation Force Impulse Imaging", IEEE Transactions on Ultrasonics, Ferroelectrics, and Frequency Control, vol. 54, No. 2, Feb. 2007, pp. 301-312 (Year: 2007).*

Nightingale, K., Acoustic Radiation Force Impulse (ARFI) Imaging: a Review, Current Medical Imaging Rev. Nov. 1, 2011; 7(4): 328-339. (Year: 2011).*

U.S. Appl. No. 14/823,957, filed Aug. 11, 2015.

Office action from counterpart Korean application No. 10-2017-0002489, filed Jan. 6, 2017, 16 total pages (including English translation).

\* cited by examiner (c) Linear fit of time to peaks

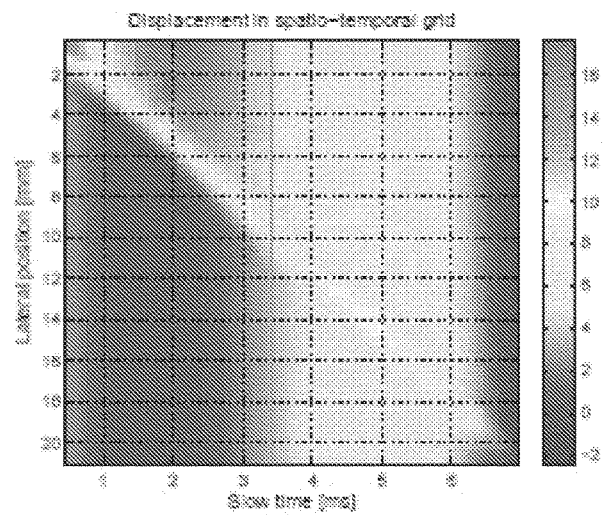
FIG. 6A
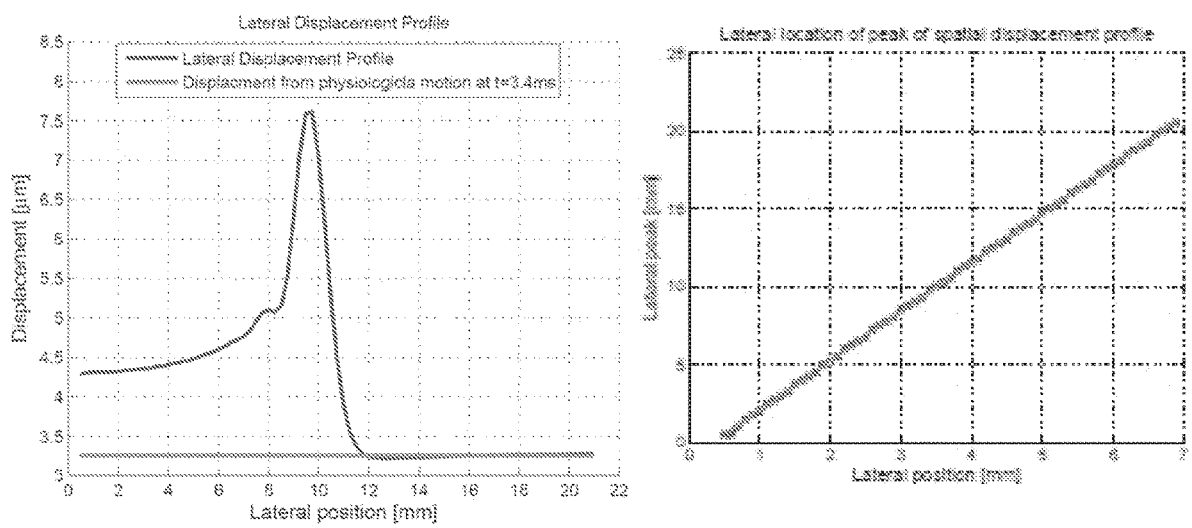
Fig. 6B
FIG. 7

US 11,717,256 B2

MOTION INDEPENDENCE IN ACOUSTIC RADIATION FORCE IMPULSE IMAGING

BACKGROUND

The present embodiments relate to acoustic radiation force impulse (ARFI) imaging. By transmitting an ARFI excitation pulse, ultrasound may be used to displace tissue through generation of a shear or longitudinal wave. The displacement resulting from the wave generated by the excitation pulse may be measured using further ultrasound scanning or tracking.

To determine the velocity of the generated shear wave in tissue, displacements are estimated over time for each location. The maximum displacement over time and/or the relative phase shift in displacement temporal profiles between locations is found. Since the cardiac and/or breathing motion of the patient causes different amount of tissue movement at different times, noise is introduced into the displacements over time. This motion may cause undesired variation in occurrence of the maximum displacement and relative phase shift, resulting in incorrect velocity determination.

BRIEF SUMMARY

By way of introduction, the preferred embodiments described below include methods, instructions, and systems for motion independent acoustic radiation force impulse imaging. Rather than rely on the displacement over time for each location, the displacements over locations for each time are used. Parallel beamforming is used to simultaneously sample across a region of interest. Since it may be assumed that the different locations are subjected to the same motion at the same time, finding a peak displacement over locations for each given time provides peak or profile information independent of the motion. The velocity or other viscoelastic parameter may be estimated from the displacements over locations.

In a first aspect, a method is provided for motion independent acoustic radiation force impulse imaging. An ultrasound scanner transmits an acoustic radiation force impulse into tissue of a patient along a first line. The ultrasound scanner detects displacements of the tissue generated in response to the transmitting with four or more receive beams at four or more locations, respectively, along each of four or more tracking lines, respectively, spaced from the first line. The detection for each of the four or more locations is repeated multiple times. For each of the multiple times, which of the four or more locations has the greatest displacement is determined. A velocity of a wave caused by the transmitting is calculated as a function of the greatest displacements from the multiple times. An image of the velocity is generated.

In a second aspect, a system is provided for motion independent acoustic radiation force impulse imaging. A transmit beamformer is configured to generate an excitation pulse. A parallel receive beamformer is configured to detect responses of tissue to a wave generated by the excitation pulse. The responses are detected at each of a plurality of locations at each of a plurality of times. A processor is configured to locate a peak in the responses over the locations at each of the times and to determine a velocity of the wave from the peaks. A display is operable to display the velocity.

In a third aspect, a non-transitory computer readable storage medium has stored therein data representing instructions executable by a programmed processor for acoustic radiation force impulse imaging. The storage medium includes instructions for: measuring, using an ultrasound scanner, displacements in response to an excitation pulse, the displacements measured simultaneously at different locations; determining a characteristic of a wave generated by the excitation pulse from a relative amount of the simultaneously measured displacements; and outputting the characteristic.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 6A is an example displacement map for position as a function of time, and FIG. 6B is a graph of displacements as a function of location for a given time in the map of FIG. 6A;

FIG. 7 is a graph showing an example estimation of velocity using the displacement peaks in spatial displacement profiles;

DETAILED DESCRIPTION OF THE DRAWINGS AND PRESENTLY PREFERRED EMBODIMENTS

Physiological motion during acoustic radiation force impulse (ARFI) scans may lead to large errors in the estimates of shear or longitudinal wave speed or other viscoelastic parameters. For ARFI imaging independent of physiological motion, an ultrasound imaging system with high parallel beamforming capability tracks the shear wave at multiple spatial locations simultaneously. The relative displacement or peak over space is used instead of over time. Since the displacements at different locations but a same time are subject to the same motion, the peak identification or displacement profile is independent of the physiological motion.

Figure 1:
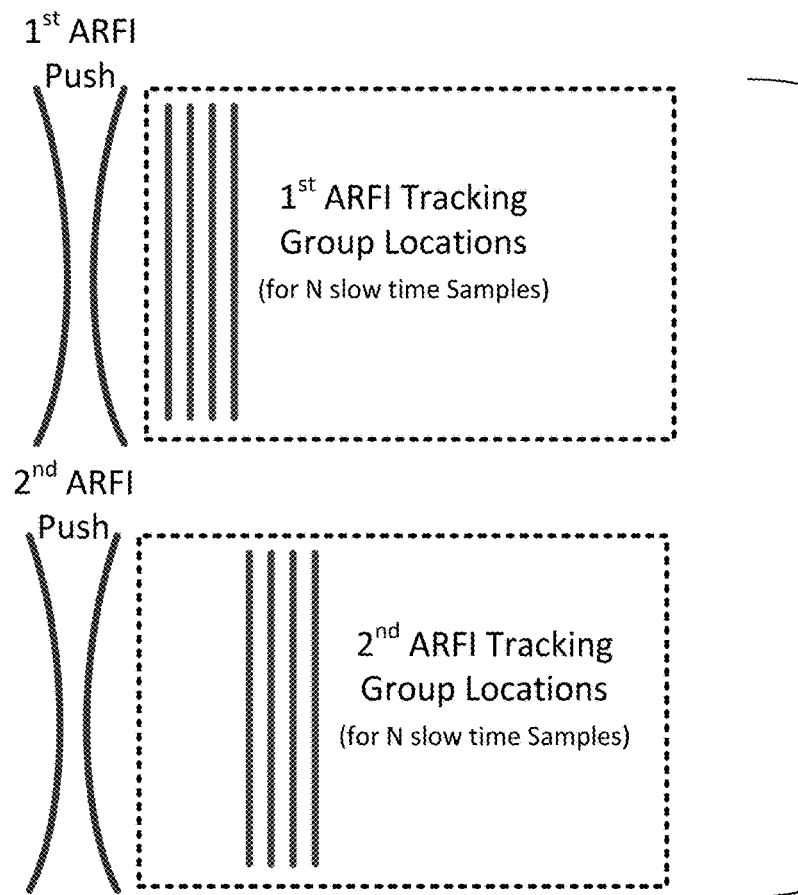
FIG. 1 illustrates an approach for sampling displacement by time.
Figure 2:
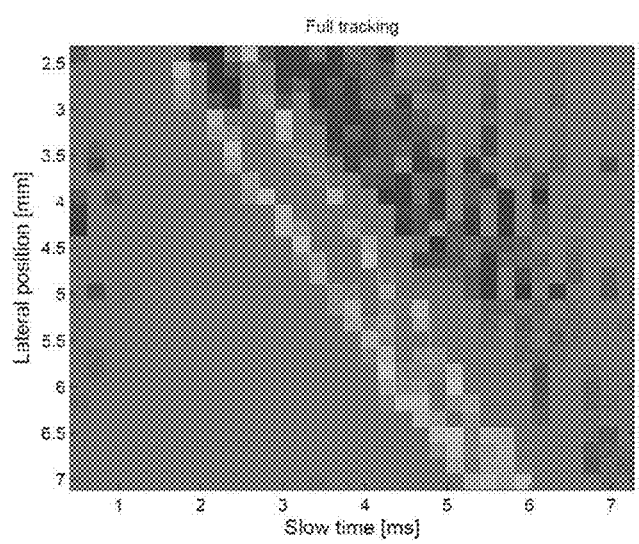
FIG. 2 is an example distribution of displacement by receive line and time for a region of interest.

FIGS. 1-4 show the effects of physiological motion where the peak is determined over time instead of space. FIGS. 1 and 2 show displacement sampling in conventional ARFI imaging. Displacements estimated over a large region with a system that has a limited beamformation require repeated ARFI pushes. FIG. 1 shows a region of interest as the dashed box. Four simultaneous receive beams along the four receive lines are shown in the box. After transmission of an ARFI excitation pulse, multiple scans of the same four lines are performed to track displacement at the four locations over time. For the temporal scanning, the same group of receive lines are scanned over a period, such as over 7 ms. With each ARFI push, only a limited number of locations are tracked over N slow time samples. Given the region of interest of FIG. 1, seven repetitions of the ARFI excitation pulse and responsive displacement monitoring at respective seven different sets of receive lines are performed.

After all the echoes from the lateral locations within the desired region have been acquired, the raw data is passed through a displacement estimation process, providing a displacement for each of the times and locations. The result is a displacement profile for each receive line location over time. FIG. 2 shows a representation of the displacement information. The x-axis is the slow time or sample rate for displacement, and the y-axis is the lateral position or receive line. The brightness is the magnitude of the displacement. For a given receive line (e.g., receive line at 3 mm), displacements over 7 ms are measured. In this example, about five displacements are measured sequentially over each millisecond. Since four simultaneous receive beams are used, the displacements over the slow time for four lateral positions are acquired at the same times. For other receive lines, the sequence of ARFI excitation pulse and tracking displacement over the 7 ms is repeated.

In the conventional approach, the maximum displacement over time is found for each lateral position. Given the distance from the ARFI focus and the time of the maximum displacement caused by the wave, a velocity of the wave traveling to that location is calculated. A velocity is determined for each location. The velocities may be displayed as spatial information or combined (e.g., averaged) to represent a velocity in that area.

This maximum displacement process, while direct, may require multiple tracking locations and consequently many ARFI pushes as represented in FIG. 1. The result is an increased risk of transducer and patient motion. Even without the repetition, the physiological motion varies over time so that the peak displacements for different times at each location are subject to different amounts of motion. This variation in displacement over time may result in the maximum peak being at a different time than if caused only by the ARFI induced wave.

Figure 3:
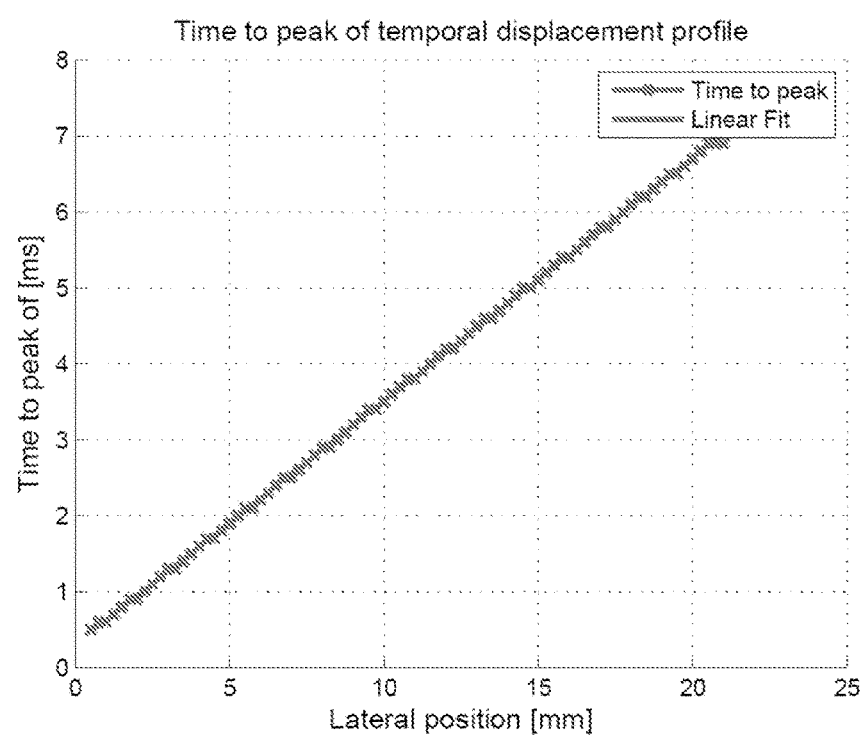
FIG. 3 is a graph showing an example estimation of velocity using displacements not subject to physiological motion.
Figure 4:
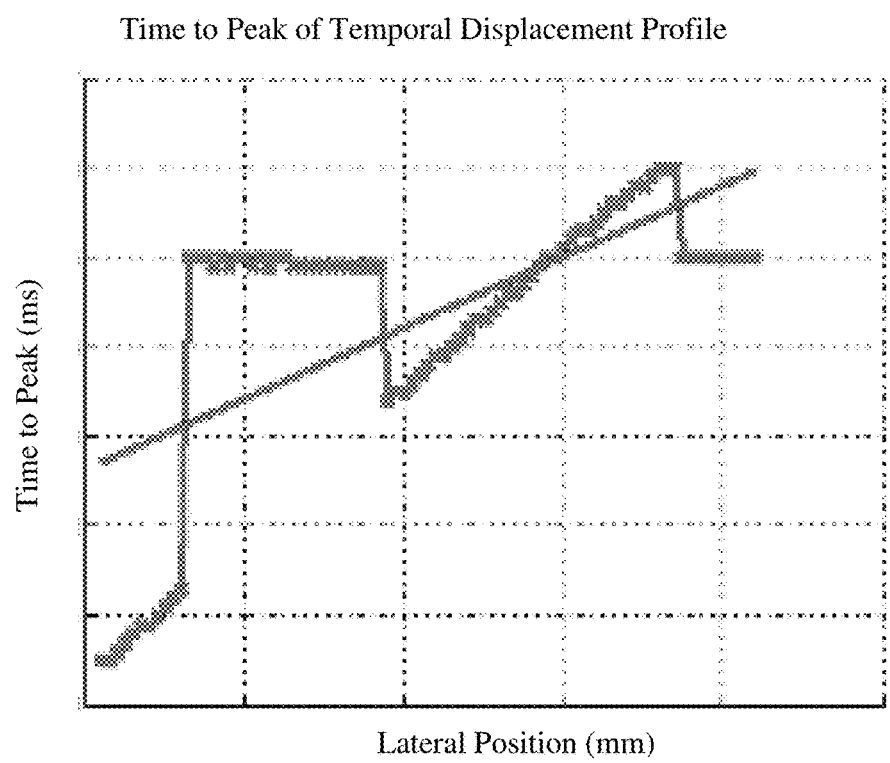
FIG. 4 is a graph showing the example estimation of velocity using the displacements of FIG. 3, but with physiological motion.

FIG. 3 shows the time of the peak displacement for each location. In FIG. 3, the slope of the fit line is directly proportional to the shear velocity estimate. This mapping of FIG. 3 is without physiological motion. The peak of the displacement profiles are correctly estimated, and the linear fit yields accurate shear wave speed. However, during in-vivo scans, physiological motion corrupts the displacement profiles over time caused by the ARFI push, which results in errors in the estimated shear wave speed. FIG. 4 shows the time-to-peak displacement for each location where physiological motion corrupts the ARFI induced displacements. The linear fit of time-to-peak estimates from the displacement profiles has a different slope than shown in FIG. 3. Because of physiological motion, several time-to peak estimates are incorrect. This leads to errors in the estimated shear wave speed.

An ultrasound imaging system with high parallel beamforming capability may sample all, most, or many of the spatial locations simultaneously. Assuming that the spatial locations within the region of interest experience the same physiological motion, then at a given slow time, the spatial displacement caused by the ARFI push is biased by the displacement caused by the physiological motion. This bias is the same for all locations at that given time. Rather than find the peak displacement over time for a location, the peak displacement over location for each given time is found. The shear or longitudinal wave motion is tracked based on the spatial distribution of the displacement rather than temporal. As a result, the peak and resulting velocity information may be independent of physiological motion.

Using peak over location for each time, the amplitude and phase information of the ARFI-induced displacements is preserved. Furthermore, no models are needed to model physiological motion. For each peak selection, the displacements are subject to the same or similar motion, so the distortion caused by motion in peak selection is minimized. The errors caused by physiological motion in shear wave speed or other viscoelastic parameters may be eliminated.

Figure 5:
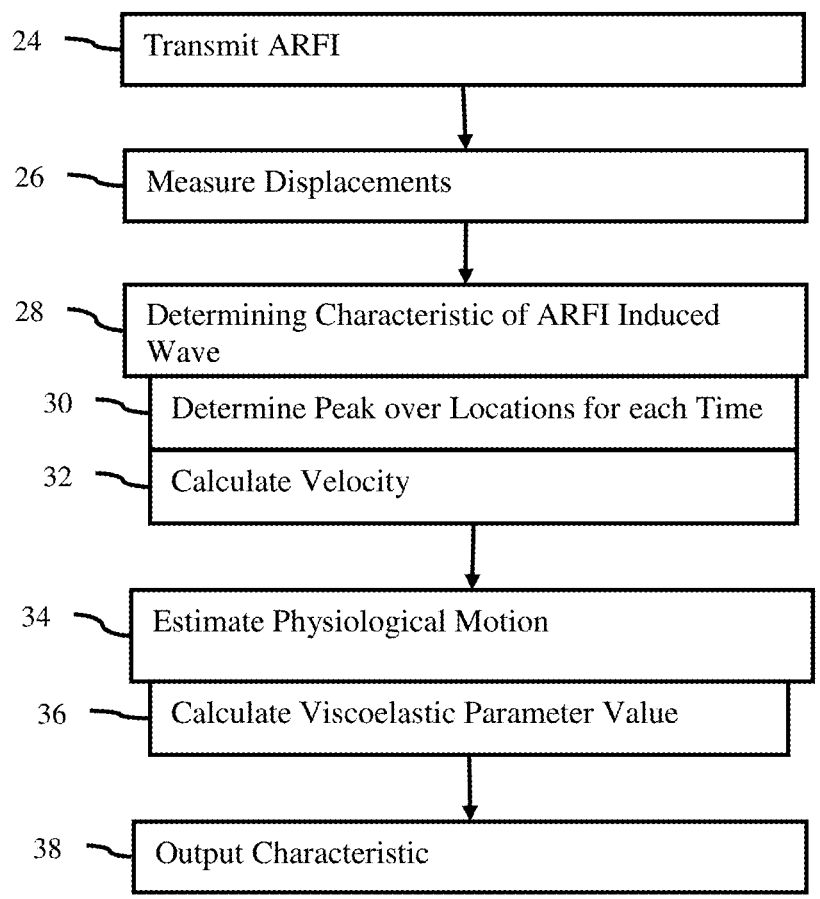
FIG. 5 is a flow chart diagram of one embodiment of a method for motion independent acoustic radiation force impulse imaging.

FIG. 5 shows one embodiment of a method for motion independent acoustic radiation force impulse imaging. Rather than finding the peak displacement over time for each location, the peak displacement over location is found for each time. As a result, the velocity estimated from the peak displacements may be more independent of motion. Extra processing to account for or remove physiological or other motion from the displacements or peaks may not be needed.

Figure 10:
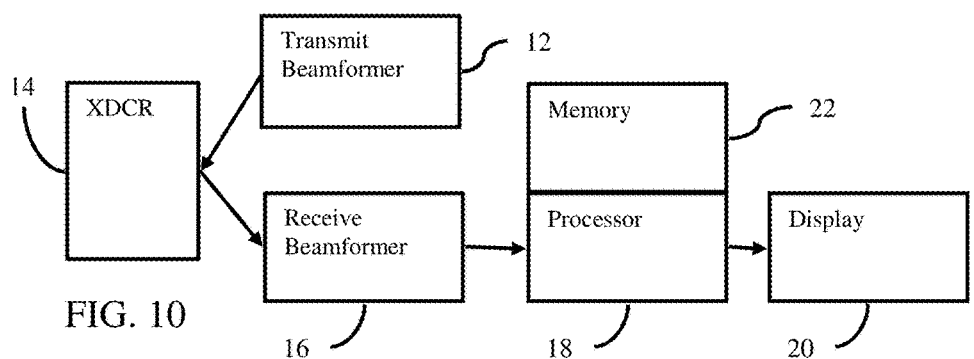
FIG. 10 is one embodiment of a system for motion independent acoustic radiation force impulse imaging.

The method is implemented by the system of FIG. 10 or a different system. For example, any now known or later developed ultrasound scanner performs acts 24 and 26. A processor, controller, or image processor of the ultrasound scanner performs acts 28-38. Alternatively, a processor of a computer or workstation separate or remote from the ultrasound scanner performs any one or more of acts 28-38. Transmit beamformers, memory, detectors and/or other devices may be used to acquire the data, perform one or more of the acts, and/or output the data. The processor may control the devices to perform the method of FIG. 5.

The acts described below are for shear wave velocity estimation. Shear waves travel laterally, so lateral estimates at a given depth or depth range are used. In other embodiments, the velocity of a longitudinal or other wave is estimated. The displacement sampling may be at locations distributed laterally and/or in depth. Any of elasticity, shear wave, or other ARFI induced wave characteristic estimation may use the peak displacement by location for a given time. Velocity is used herein as the characteristic, but other characteristics parameterizing the tissue response to the acoustically induced wave may be estimated, such as Young's Modulus, strain, strain rate, or shear modulus.

Additional, different, or fewer acts may be provided. For example, the method is performed without outputting velocity in act 38. As another example, acts 24-30 represent one example sequence for determining the velocity of act 32. Other acts or sub-sets may be used to determine the velocity. As another example, acts 34 and 36 are not performed. The motion may remain in the displacements as the use of peak displacement over space removes the motion-induced error in the velocity estimation. In other examples, filtering or other data processing is applied to the displacements.

The acts are performed in the order described or shown, but may be performed in other orders. For example, act 24 shows transmission of a single excitation pulse. Act 24, and the responsive acts 26, 28 and 30, may be repeated to measure over a larger region of interest. This repetition occurs before the determination of act 32. As another example, the physiological motion is estimated in acts 34 and removed from the displacements prior to act 28.

In act 24, an ARFI push is transmitted by the ultrasound scanner into tissue of a patient. The transmission is a transmit beam focused at a depth or range of depths. The ARFI transmit beam is transmitted along a transmit scan line. The focal depth is on the transmit scan line.

An array of elements in an ultrasound transducer transmits the ARFI beam converted from electrical waveforms. The acoustic energy is transmitted to the tissue in a patient. The acoustic waveform is transmitted for generating a shear, longitudinal, or other wave as stress to displace tissue. The excitation is an ultrasound excitation pulse. The acoustic energy is focused to apply sufficient energy to cause generation of one or more waves that then travel through the tissue from the focal location. The acoustic waveform may itself displace the tissue. Other sources of stress may be used.

To generate the wave, high amplitude or power excitations are desired. For example, the excitation has a mechanical index of close to but not exceeding 1.9 at any of the focal locations and/or in the field of view. To be conservative and account for probe variation, mechanical index of 1.7 or other level may be used as the upper limit. Greater (e.g., MI exceeding 1.9) or lesser powers may be used.

The excitation pulse is transmitted with waveforms having any number of cycles. In one embodiment, one, most, or all of the waveforms for a pushing pulse transmit event have 100-2,000 cycles. The number of cycles is tens, hundreds, thousands, or more for the continuous transmit waveforms applied to the elements of the array for the excitation pulse. Unlike imaging pulses that are 1-5 cycles, the ARFI excitation or pushing pulse has a greater number of cycles to generate sufficient stress to cause the wave for displacing tissue with an amplitude sufficient to detect.

The shear wave or waves are generated at the focal region and propagate laterally, axially, and/or in other directions from the focal region. The waves may travel in multiple directions. The waves reduce in amplitude as the waves travel through the tissue.

In one embodiment, a single excitation pulse is generated. In other embodiments, a pattern of excitation pulses may be generated. Any pre-determined pattern may be used, such as pulses overlapping in time but with different frequency, focus, or other characteristic. One example pattern is a sequence of excitations with a short pause between the pulses. Short may be less than a time for reverberation reduction and/or less than a length of an excitation pulse. The pattern provides different excitations prior to tracking in act 26. Because of the pattern, a series of shear or other waves are generated. This results in a pattern of waves and corresponding displacements at different locations. This pattern may be used to provide additional peaks or other information for estimating a characteristic of the tissue and/or wave.

In act 26, the ultrasound scanner measures or detects displacements of the tissue generated in response to the ARFI transmission. The response of tissue to the excitation is detected and used to measure the displacement.

The generated wave is tracked. The wave is generated in response to the ARFI transmission. The tissue response is a function of the wave created by the ARFI beam and the tissue characteristics. The wave is tracked at multiple locations. For a shear wave, the wave is tracked at laterally spaced locations of a same depth or depth range. The tracking detects the effects of the wave rather than specifically identifying where the wave is located at a given time.

The tracking is performed by ultrasound scanning. To detect the displacement, ultrasound energy is transmitted to the tissue undergoing displacement, and reflections of the acoustic energy are received. To detect tissue response to waves in a region of interest, transmissions are made to the region, and detection is performed in the region. These other transmissions are for detecting the waves or displacement rather than causing the wave or displacement. The transmissions for detection may have lower power and/or short pulses (e.g., 1-5 carrier cycles).

B-mode or other scanning along multiple receive lines is performed to track. The displacement indicates the effects of the wave, such as no displacement indicating an absence of the wave and a displacement indicating tissue movement caused by the wave. As the wave passes a given location, the tissue displaces by an amount or distance that increases to a peak amount and then decreases as the tissue returns to rest. Similarly, for a given time, one location may be displaced more than other locations since the peak of the wave is located at or by that location. The tracking may detect the effects of the wave at any stage (i.e., no wave, increasing displacement, maximum, or decreasing displacement).

The tissue is scanned multiple times to determine the displacement, such as scanning a region at least twice. To determine displacement at one time, a sample echo return is compared to a reference. The displacement is provided as the difference or offset from the reference scan (first scan) and a later scan (displacement measure). The tissue is scanned using any imaging modality capable of scanning for displacement during the tissue's response, such as during or after application of the ARFI excitation pulse.

For ultrasound scanning, the wave is detected at locations adjacent to and/or spaced from the focal region for the ARFI excitation pulse. The displacements are sampled at various receive lines (e.g., FIG. 1 shows four receive lines as parallel vertical lines). Non-parallel and/or non-vertical receive lines may be used.

Any number of lateral locations may be used, such as twenty-eight. The transmissions for detection may have a wider beam profile along at least one dimension, such as laterally, for simultaneously forming receive samples along a plurality of scan lines (e.g., receive beamforming simultaneously along four or more receive lines). Any number of simultaneous receive beams may be formed, such as four, eight, sixteen, thirty-two, sixty-four, or more. In one embodiment, the parallel receive beamformer forms beams to sample the entire region of interest, such as the twenty-eight lateral locations. For larger regions of interest, the receive beam spacing is shifted to sample across the full extent of the region in response to each tracking transmission. Parallel beamformation is used to sample across the entire region of interest. For shear wave tracking, four or more receive beams sample four or more locations along four or more tracking lines spaced from the ARFI transmission line or focal point. Each sample location is at a same depth along the tracking lines. Using parallel beamformation, the different locations are sampled simultaneously.

The tracking transmissions and corresponding receive beams are performed sequentially. For a given receive event (i.e., receiving echoes responsive to a given transmission for tracking), N receive beams are formed. To sample over time, the tracking transmission and receiving of echoes from the multiple locations simultaneously is repeated.

A region of interest is monitored to detect the wave. The region of interest is any size. For example, the wave is detected along various depths of one or more lines in ARFI imaging. As another example, the displacements are tracked at each of a plurality of laterally spaced locations for a limited depth in shear wave imaging.

The transmission and reception for detection or tracking are performed multiple times for each receive line to determine change due to displacement over time. Due to parallel beamforming, the transmission and reception for detection or tracking allow for detection of displacements at different locations at a same time. Any transmission and reception sequence may be used.

For determining displacement, a reference scan of all of the receive lines in the region of interest is performed prior to the ARFI transmission of act 24. After the ARFI transmission of act 24, N simultaneous receive lines are used. N is a multiple of two or more and does not exceed the number of simultaneous receive beams for which the receive beamformer is capable. For example, N is an integer greater than 8, 16, 32, 64, or other number. The tracking allows for measuring N displacements per receive event for N tracking lines, respectively, at one time, and repeating the measuring for the N tracking lines at other times.

The samples or measured tissue responses are used to determine displacement in act 26. The displacement at each of the locations for any time for which an echo was sampled is determined. For the shear wave imaging, the displacement at the depth or depth range along each tracking line is determined.

The displacement is calculated from the ultrasound scan data. The tissue moves between two scans. A reference scan is performed before the ARFI transmit of act 24 and/or after the generated wave has passed the location. The data of the sample scan or the reference scan is translated or shifted in one, two, or three dimensions relative to the data in the other scan. For each possible relative position, an amount of similarity is calculated for data around the location. The amount of similarity is determined with correlation, such as a cross-correlation. A minimum sum of absolute differences or other function may be used. The spatial offset with the highest or sufficient correlation indicates the amount of displacement for a given location. In other embodiments, a phase offset of data received from different times is calculated. The phase offset indicates the amount of displacement. In yet other embodiments, data representing a line (e.g., axial) at different times is correlated to determine a shift for each of a plurality of depths along the line.

A single ARFI excitation pulse is used to estimate displacements for all the locations. FIG. 6A shows estimation of all locations in a 22 mm region of interest at a given depth. By repeating the displacement detection using samples from the repeated tracking, the displacements for all of the locations are determined for each of multiple times (e.g., sampling every 0.1 ms over 0-7 ms in FIG. 6A).

The excitation pulse and tracking may be repeated for different depths. To monitor a larger lateral region, excitation pulses and tracking may repeated for other locations.

FIG. 6A shows the displacements as gray-scale amplitude for the various locations and times. A bar on the right indicates the mapping of displacement to color (shown as gray level). In general, the wave causes a ridge of greater displacements that occur on one lateral side early and the other lateral side later. The wave propagates over time across the region of interest, occurring earlier at locations closer to the ARFI focus.

Since time of maximum displacement for a given location is unknown, the sampled displacements may or may not be associated with a maximum displacement caused by the wave passing the tissue. FIG. 6B shows a graph of the displacements as a function of location for a given time. In the example of FIG. 6B, the time is 3.4 ms. FIG. 6A shows a vertical line at 3.4 ms. For 3.4 ms, FIG. 6B shows the wave causing displacements with greater magnitude starting from 0 mm and increasing to a peak at about 9 mm, and then decreasing until a steady state around 11 mm. The steady state shows displacements caused by other factors than the wave or displacements without any contribution by the wave. If the profile of displacements as a function of location were for a later time, then the peak may be shifted to a further location and the steady state may begin to occur at the closer (e.g., lower position) locations.

FIG. 6B shows one peak. Where a pattern of excitation pulses are used, multiple waves may be generated. Depending on whether the multiple excitation pulses have a same or different focal location and/or relative timing and the time being sampled, more than one peak may occur in the displacement as a function of location profile. The displacements caused by the pattern of waves are detected after the pattern of excitation pulses occurs (e.g., after the multiple shear waves are generated).

In act 28, a processor determines a characteristic of the tissue and/or wave or waves generated by the excitation pulse or pulses. Any characteristic may be determined. For example, the shear speed or velocity is determined. In other examples, other viscoelastic parameters (e.g., Young's Modulus) are determined.

In the embodiment of FIG. 5, the determination is represented as acts 30 and 32. Additional, different, or fewer acts may be provided. For example, to determine some viscoelastic parameters, a Fourier transform is applied to the displacements, such as the displacement profile over time. Since the temporal response is used, act 34 is performed prior to calculation of the parameter in act 36, which replaces act 32.

In act 30, the processor determines the characteristic from a relative amount of the simultaneously measured displacements. The displacements from different locations are compared. In one embodiment, any peaks in the displacement profile over location are identified. For each given sample time or slow time, the displacements are compared to find the greatest displacement. In other embodiments, a curve is fit to the displacements and the location of the peak in the curve is found. The peak of a fit curve may be between two sampling locations. Other approaches may be used. The various approaches locate the greatest peak or different peaks in the simultaneously measured displacements. The peak or peaks are across the locations for a given time. The wave is located from the spatial distribution of the displacements. The peak indicates the location of the wave at that time.

As shown in FIG. 6B, one peak is provided at about 9 mm. Since the peak is found across locations instead of time, the motion (e.g., horizontal line at about 3.3 µm) contributes a same offset to all of the displacements, so does not affect the shape of the profile or location of the peak. The physiological motion biases the profile, such as biasing by adding displacement in this example.

The analysis is repeated for one or more times. The peak or peaks are determined for each of multiple times. FIG. 7 shows the location of the peak mapped to the times. As compared to FIG. 3, the axes of FIG. 7 are reversed or flipped. In this embodiment, the location of the peak displacement at each time is found. In alternative embodiments, only one, two or other sub-sets of the sample times are used.

If a pattern of excitations and resulting waves are used, more than one peak may be located for some or all of the times. This resulting pattern of peaks may be used to estimate the characteristics.

In alternative embodiments, the peak or peaks are not identified. Instead, the relative displacements as a function of location (e.g., the displacement profile) are used to calculate the characteristic without determining the peak.

In act 32, the characteristic, such as velocity, is calculated. The processor calculates the velocity of the wave caused by the ARFI transmission. Other characteristics may be calculated, but velocity is used in the discussion below.

The velocity is calculated from the peak or peaks. The greatest or locally greater displacement over location is used to calculated velocity. In one embodiment, the calculation is simply the sample time for the peak and the distance of the location of the peak from the ARFI focal position. This calculation may be repeated for other times, providing velocities at different locations of peaks. Alternatively, the locations of peaks from different times are used to estimate a velocity for the tissue region or region of interest.

In one embodiment represented in FIG. 7, the locations of the peak as a function of time are used. A line is fit to the locations of the peaks as a function of time. Any fitting may be used, such as a least squares fit. By fitting a line to the greatest of the displacements over time, the velocity may be calculated from the slope or inverse of the slope. In this case, the greatest of the displacements is represented by the locations of the peak displacements at different times. A straight line is fit to the locations as a function of time. Accurate estimates of the shear wave speed are found by fitting a line based on the lateral positions of the peaks of the displacement profiles at multiple slow times. For shear-wave speed imaging, it is sufficient to use the spatial profiles with no physiological motion compensation.

Since the peaks are independent of the physiological motion, errors caused by the physiological motion variation over time are reduced or eliminated. The peaks are found across space for each given time, making the location of the peaks independent of motion. Comparatively, finding the peak for each location over time subjects analysis to variation in displacements caused by physiological motion. As a result, the detected peak may be at a time different than the peak caused by the wave.

The characteristic is alternatively calculated using phasing. The profiles of displacements as a function of locations for different times are correlated. The phase offset and the temporal sampling difference may be used to determine the velocity.

In another embodiment, the fitting is directly to the map of displacements (e.g., see FIG. 6A) without identifying peaks. The fitting may be weighted by the magnitudes of the displacements. The displacement magnitudes may be adjusted to account for wave attenuation as a function of distance before the displacement weighted fitting. Once fit, the line provides a slope or angle used to calculate the velocity. By using parallel beamforming across the entire region of interest, the resulting fit may be less susceptible to errors caused by physiological motion.

Figure 8:
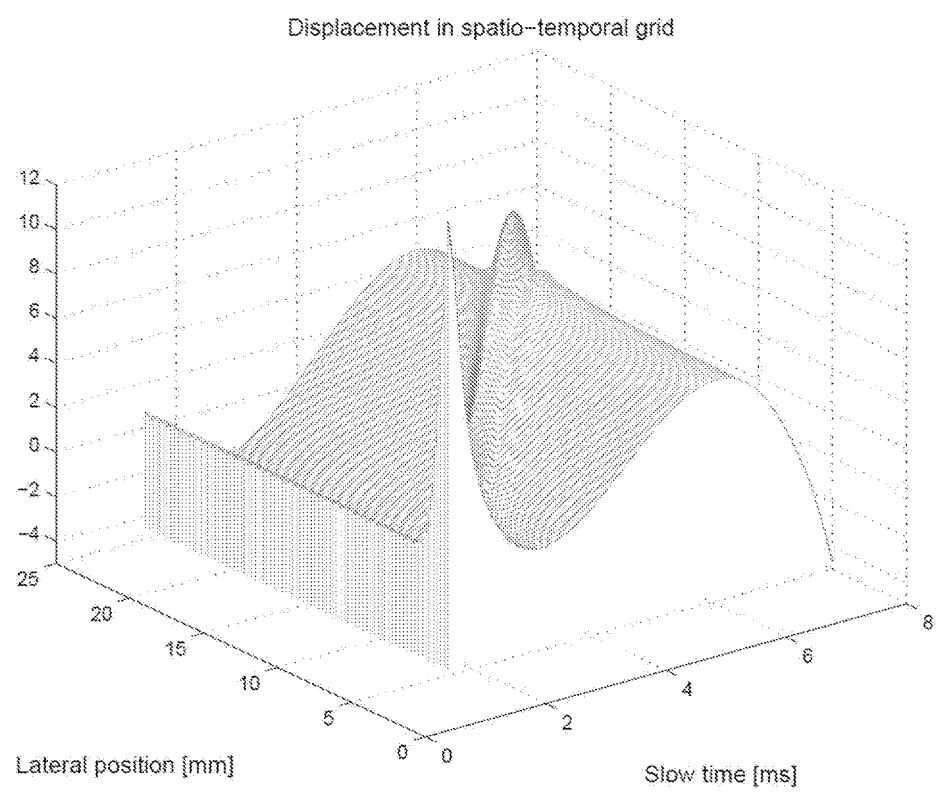
FIG. 8 shows an example grid of displacements as a function of position and time.
Figure 9:
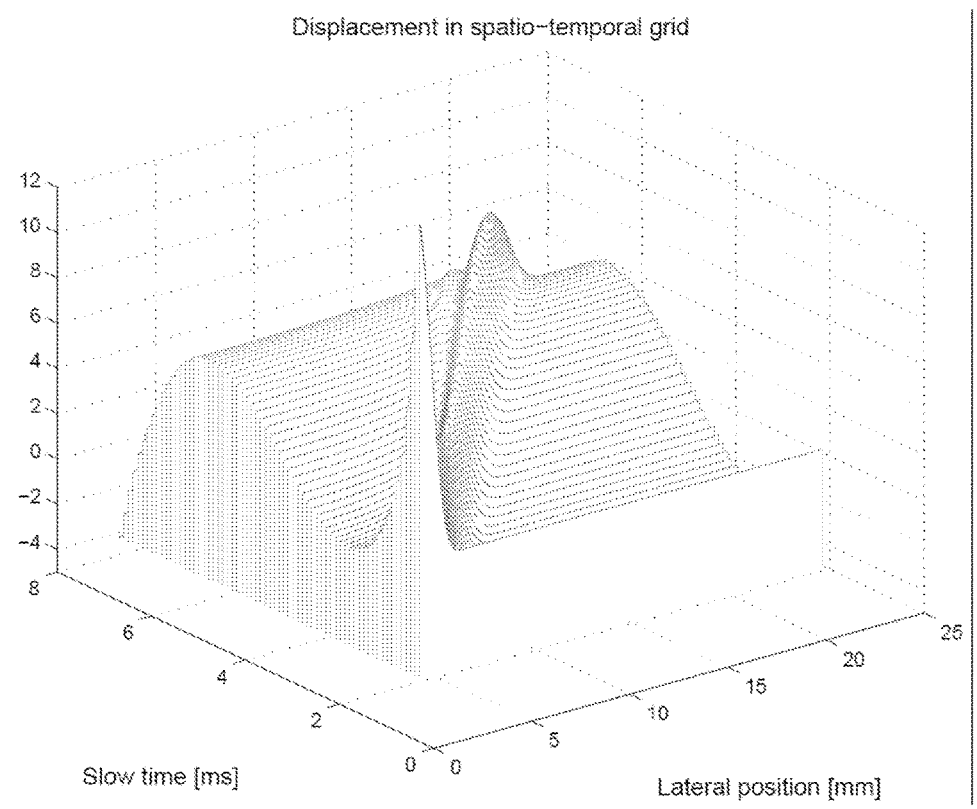
FIG. 9 shows an example grid of the displacements of FIG. 8 but as a function of time and position.

FIG. 8 show an example surface or three-dimensional plot of the displacement over position as a function of time. This arrangement represents motion independent velocity determination. FIG. 9 shows an example surface or three-dimensional plot of displacement over time as a function of position. The arrangement represents finding the peak over time rather than location. While both FIGS. 8 and 9 show a similar ridge, the reversal of the axes enabled by parallel beamforming allows estimation independent of physiological motion.

Where a pattern of waves is generated, the fitting may be different. For each time, multiple peaks are provided. The peaks may be distinguished from each other so that the different waves are separated. The pattern of wave generation (e.g., focal location and/or timing) is used to distinguish. Velocities for each wave are calculated separately. The resulting velocities may be combined. Alternatively, template patterns are matched or fit to the pattern of locations of peaks. The best-fit pattern is associated with a pre-determined velocity. Other approaches may be used, such as using a separation of the locations of peaks at a given time to indicate the velocity.

In act 34, the processor estimates physiological motion. The contribution of the physiological motion to the displacements may be determined. To estimate the physiological motion, a steady state offset in the displacements is identified. As shown in FIG. 6B, displacement from physiological motion may be estimated from the bias of the spatial profile at a time. A lowest displacement constant over a threshold distance (e.g., 3 or 5 mm) is found. That lowest displacement represents the bias or physiological motion. In the example of FIG. 6B, the bias due to physiological motion is about 3.3 μm.

The physiological motion may vary over time. Since displacement profiles as a function of location are created for different times, the bias may be found for each of multiple slow times. The bias for each slow time is the physiological motion for that time. Variation across time may be used to find the period or other motion information.

The physiological motion may be removed from the displacements. The offset or bias for each time is subtracted from the displacements for that time. The removal may occur prior to identifying the peaks. Alternatively, the removal occurs after finding the peaks, such as where the displacements are to be used in other analysis.

In one embodiment, the bias is removed to estimate other viscoelastic parameters than velocity. Displacement from physiological motion is first estimated from each spatial profile and subtracted prior to further displacement data processing. The further data processing may be calculation of a value of a viscoelastic parameter in act 36. For example, a Fourier transform is applied to the displacements after removal of the physiological motion. The value of the viscoelastic parameter is derived from the transformed displacements without or with reduced errors from physiological motion contribution.

In act 38, the processor outputs the characteristic. The output is to a memory, over a network, or on a display. For display, the velocity or other characteristic of the wave is displayed as a value in numbers and/or letters (e.g., "2.0 m/s"). Alternatively, a graphic representation of the velocity or characteristic is used, such as a pointer on a scale or a bar graph. The velocity may be displayed as a color or other indexed symbol.

In one embodiment, a single velocity is determined. A user positions a pointer on an image. In response, the ultrasound scanner outputs a velocity calculated for that point (e.g., the point is used for the ARFI focus and the velocity for a small region next to or around the point is calculated). In other embodiments, more than one velocity is output. The velocities at different locations are found. For example, a curve is fit, and the slope of the curve at different locations represents the different velocities. As another example, different measurements are made for different locations.

An image of the velocity is a display of a single velocity or a display of multiple velocities. For velocities measured at different locations, the image may include a one, two, or three-dimensional representation of the velocity or characteristic as a function of space or location. For example, the shear velocity throughout a region is displayed. Shear velocity values modulate color for pixels in a region in a gray-scale modulated B-mode image. The image may represent displacement information, such as shear or moduli (e.g., the shear moduli) for different locations. The display grid may be different from the scan grid and/or grid for which displacements are calculated. Color, brightness, luminance, hue, or other characteristic of pixels is modulated as a function of the information derived from the displacements.

FIG. 10 shows one embodiment of a system for motion independent acoustic radiation force impulse imaging. Ultrasound generates tissue displacement, such as through creation of a shear or longitudinal wave, and scan data responsive to the tissue responding to the displacement is used to determine velocity or other characteristic of the wave in the tissue. To avoid errors due to undesired motion, the velocity or other characteristic uses relative displacements as a function of location for each time rather than as a function of time for each location.

The system is a medical diagnostic ultrasound imaging system. In alternative embodiments, the system is a personal computer, workstation, PACS station, or other arrangement at a same location or distributed over a network for real-time or post acquisition imaging.

The system implements the method of FIG. 5 or other methods. The system includes a transmit beamformer 12, a transducer 14, a receive beamformer 16, an image processor 18, a display 20, and a memory 22. Additional, different or fewer components may be provided. For example, a user input is provided for manual or assisted designation of a region of interest for which information is to be obtained.

The transmit beamformer 12 is an ultrasound transmitter, memory, pulser, analog circuit, digital circuit, or combinations thereof. The transmit beamformer 12 is configured to generate waveforms for a plurality of channels with different or relative amplitudes, delays, and/or phasing. The waveforms are generated and applied to elements of the transducer 14 with any timing or pulse repetition frequency. For example, the transmit beamformer 12 generates a excitation pulse for generating a shear wave in a region of interest and generates corresponding transmissions for tracking resulting displacements with ultrasound. The transmit beamformer 12 may be configured to generate a sequence or other combination of excitation pulses for generating multiple waves to be tracked.

The transmit beamformer 12 connects with the transducer 14, such as through a transmit/receive switch. Upon transmission of acoustic waves from the transducer 14, one or more beams are formed during a given transmit event. The beams are excitation pulses and/or tracking beams. For scanning tissue displacement, a sequence of transmit beams are generated to scan a one, two or three-dimensional region. Sector, Vector®, linear, or other scan formats may be used. The scanning by the transmit beamformer 12 occurs after transmission of the excitation pulse, but may include scanning for reference frames used in tracking before transmitting the excitation pulse. The same elements of the transducer 14 are used for both scanning and displacing tissue, but different elements, transducers, and/or beamformers may be used.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. For example, the transducer 14 is a one-dimensional PZT array with about 64-256 elements.

The transducer 14 connects with the transmit beamformer 12 for converting electrical waveforms into acoustic waveforms, and connects with the receive beamformer 16 for converting acoustic echoes into electrical signals. The transducer 14 transmits the excitation pulse and tracking beams. The waveforms are focused at a tissue region or location of interest in the patient. The acoustic waveforms are generated in response to applying the electrical waveforms to the transducer elements. For scanning with ultrasound to detect displacement, the transducer 14 transmits acoustic energy and receives echoes. Receive signals are generated in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form multiple receive beams in response to each transmission for detection of the tissue response or tracking. Dynamic focusing on receive may be provided. Where only one depth or depth range is of interest, dynamic focusing may or may not be provided. The receive beamformer 16 outputs data representing spatial locations using the received acoustic signals. Relative delays and/or phasing and summation of signals from different elements provide beamformation. In alternative embodiments, the receive beamformer 16 is a processor for generating samples using Fourier or other transforms.

For parallel receive beamformation, the receive beamformer 16 is a parallel receive beamformer configured to include additional sets of channels and corresponding summers. Each channel applies relative delays and/or phasing to form a beam with the summer. The receive beamformer 16 may have any number N of sets of channels and summers. N is an integer greater than 1, such as N=8-132, for forming a corresponding number of beams simultaneously or in response to a same tracking transmit beam. The receive beams may be formed as a regular sampling of space in a region of interest. The locations are simultaneously sampled by respective receive beams formed by the receive beamformer 16.

The receive beamformer 16 may include a filter, such as a filter for isolating information at a second harmonic or other frequency band relative to the transmit frequency band. Such information may more likely include desired tissue, contrast agent, and/or flow information.

The receive beamformer 16 outputs beam summed data representing spatial locations. Data for a single location, locations along a line, locations for an area, or locations for a volume are output. The data may be for different purposes. For example, different scans are performed for B-mode or tissue detection than for shear or longitudinal wave detection. Alternatively, the B-mode data is also used to determine displacement caused by a shear or longitudinal wave.

The receive beamformer 16 is configured to detect responses of tissue to the wave generated by the excitation pulse. The tissue is scanned. The receive signals generated by the receive beamformer 16 represent response from the tissue at the time of sampling. Using parallel receive beamformation, different locations are sampled simultaneously. Since the tissue is subject to any displacement caused by the wave, the tissue response is captured by the sampling. The acoustic responses are detected at each of a plurality of locations at each of a plurality of times. The responses of the tissue to more than one wave may be detected.

The processor 18 or a separate beamformer controller configures the beamformers 12, 16. By loading values into registers or a table used for operation, the values of acquisition parameters used by the beamformers 12, 16 for ARFI imaging are set. Any control structure or format may be used to establish the ARFI imaging sequence. The beamformers 12, 16 are caused to acquire data for ARFI imaging at a frame rate and/or with a resolution. Different values of one or more acquisition parameters may result in a different frame rate and/or resolution.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for calculating displacements from responses output by the receive beamformer 16.

In one embodiment, the processor 18 includes one or more detectors and a separate processor. The separate processor is a control processor, general processor, digital signal processor, graphics processing unit, application specific integrated circuit, field programmable gate array, network, server, group of processors, data path, combinations thereof or other now known or later developed device for determining displacement and/or calculating velocity from displacements. The processor 18 is configured by software and/or hardware to perform the acts.

In one embodiment for ARFI imaging, the processor 18 estimates tissue displacement for each of a plurality of lateral locations. The displacements occurring at a same time are estimated. Estimates of displacements for the various locations are formed for each of the sample times. The data output by the receive beamformer 16 is used to determine the displacement at different locations for each of a plurality of times. The displacements may be obtained by correlating or otherwise determining level of similarity between reference data and data obtained to represent the tissue at a time.

The processor 18 is configured to calculate tissue characteristics form the displacements of the tissue at different locations. For example, a shear velocity is calculated from the displacements. In another example, the processor 18 calculates viscosity and/or modulus. The processor 18 may calculate other properties, such as strain or elasticity.

The processor 18 is configured to estimate the velocity or other characteristic from the relative displacements over space. One or more peaks in a profile of the displacements as a function of location are found. Using parallel beamforming, the displacements for the various locations at a given time are subject to the same or similar motion. By finding peaks over space for each time, the variability of the motion may be ignored.

The processor 18 is configured to determine the velocity of the wave in the tissue from the peaks. A line or pattern is fit to the peaks by location as a function of time. The slope of the line, slopes of lines in the pattern, or label with the pattern indicates the velocity. Other calculations for velocity may be used. Pattern matching, phasing, or other approaches using the simultaneously acquired displacements for each time may be used.

In other embodiments, the processor 18 is configured to identify the part of the displacements caused by physiological motion for each time. This undesired motion may be removed. As a result, viscoelastic parameters relying on variance over time of the displacements may be calculated with minimal influence by physiological motion.

The processor 18 generates and outputs image or display values mapped from the characteristic to the display 20. For example, the velocity, shear modulus or other value is determined. A text or numerical indication of the characteristic is displayed to the user. A graph of the characteristic over time may be displayed.

In one embodiment, the property is displayed as a function of location. Values, graphs, and/or tissue representations may be displayed using the velocity at different locations. For a representation of the tissue, the magnitude of the wave or tissue characteristic modulates the color, hue, brightness, and/or other display characteristic for different pixels representing a tissue region. The processor 18 determines a pixel value (e.g., RGB) or a scalar value converted to a pixel value. The image is generated as the scalar or pixel values. The image may be output to a video processor, look-up table, color map, or directly to the display 20.

The display 20 is a CRT, LCD, monitor, plasma, projector, printer, or other device for displaying an image or sequence of images. Any now known or later developed display 20 may be used. The display 20 is operable to display one image or a sequence of images. The display 20 displays two-dimensional images or three-dimensional representations. The display 20 displays one or more images representing the tissue characteristic or other information derived from displacements. As an example, a velocity associated with a location indicated on a two-dimensional image or three-dimensional B-mode representation is displayed. Alternatively or additionally, the image is a graph.

The processor 18, the receive beamformer 16, and the transmit beamformer 12 operate pursuant to instructions stored in the memory 22 or another memory. The instructions configure the system for performance of the acts of FIG. 5. The instructions configure the processor 18, the receive beamformer 16, and/or the transmit beamformer 12 for operation by being loaded into a controller, by causing loading of a table of values (e.g., elasticity imaging sequence), and/or by being executed. The transmit beamformer 12 is configured by the instructions to cause generation of an excitation beam and tracking beams. The receive beamformer 16 is configured by the instruction to acquire data for tracking. The processor 18 is configured to estimate displacements and determine the velocity from peaks detected as a function of location for each of various times.

The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for motion independent acoustic radiation force impulse imaging, the method comprising:
    transmitting, with an ultrasound scanner, an acoustic radiation force impulse into tissue of a patient along a first line;
    detecting, with the ultrasound scanner, displacements of the tissue generated in response to the transmitting with four or more receive beams at four or more locations, respectively, along each of four or more tracking lines, respectively, spaced from the first line, the detecting for each of the four or more locations repeated multiple times;
    for each of the multiple times, locating a greatest of the displacements of the four or more locations by comparison of the displacements of the four or more locations;
    calculating a velocity of a wave caused by the transmitting, the velocity being calculated as a function of the greatest displacements from the multiple times;
    generating an image of the velocity.

2. The method of claim 1 wherein transmitting the acoustic radiation force impulse comprises transmitting the acoustic radiation force impulse as focused at a depth along the first line, and wherein detecting comprises tracking the wave at the depth on the tracking lines, the wave comprising a shear wave.

3. The method of claim 1 wherein detecting the displacements with the four or more receive beams at four or more locations comprises detecting sixteen or more receive beams at sixteen or more respective locations.

4. The method of claim 1 wherein detecting the displacements with the four or more receive beams comprises detecting with simultaneous parallel beamforming.

5. The method of claim 1 wherein locating the greatest of the displacements comprises determining an amount of shift of tissue from a reference.

6. The method of claim 1 wherein locating the greatest of the displacements comprises locating the wave from a spatial distribution of the displacements.

7. The method of claim 1 wherein calculating the velocity comprises fitting a line to the greatest of the displacements as a function of time and calculating the velocity as a slope of the line.

8. The method of claim 1 wherein calculating the velocity comprises calculating such that errors in the displacements caused by physiological motion are eliminated.

9. The method of claim 1 further comprising estimating contribution of physiological motion to the displacements.

10. The method of claim 9 wherein estimating the contribution comprises identifying a steady state offset in the displacements as a function of the locations.

11. The method of claim 10 further comprising removing the offset from the displacements and calculating a viscoelastic parameter from a Fourier transform of the displacements after the removal.

12. The method of claim 1 wherein the transmitting of the acoustic radiation force impulse comprises transmitting the acoustic radiation force impulse as one such impulse in a pattern of multiple impulses with the detecting being performed in response to the pattern, and wherein the locating of the greatest of the displacements comprises determining multiple peaks in the displacements as a function of the location for each of the multiple times.

13. The method of claim 12 wherein calculating the velocity comprises matching the pattern to the multiple peaks.

14. A system for motion independent acoustic radiation force impulse imaging, the system comprising:
    a transmit beamformer configured to generate an excitation pulse;
    a parallel receive beamformer configured to detect responses of tissue to a wave generated by the excitation pulse, the responses detected at each of a plurality of locations at each of a plurality of times;
    a processor configured to locate a peak in the responses over the locations at each of the times and determine a velocity of the wave from the peaks; and
    a display operable to display the velocity.

15. The system of claim 14 wherein the parallel receive beamformer is configured to simultaneously receive beamform along N receive lines where N is an integer greater than one and equal to the plurality of the locations.

16. The system of claim 14 wherein the processor is configured to calculate displacements from the responses, wherein the processor is configured to locate the peak as a greatest of the displacements over the locations at the respective time, and wherein the processor is configured to determine the velocity from a line or pattern fit to the greatest of the displacements over time.

17. The system of claim 14 wherein the transmit beamformer is configured to generate the excitation pulse in a sequence of generated pulses, wherein the parallel receive beamformer is configured to detect responses to the wave and other waves generated by the sequence after completion of the sequence, and wherein the processor is configured to locate the peak and other peaks in the responses at each of the times and determine the velocity from the peak and the other peaks of each time.

18. A non-transitory computer readable storage medium having stored therein data representing instructions executable by a programmed processor for acoustic radiation force impulse imaging, the storage medium comprising instructions for:
    measuring, using an ultrasound scanner, displacements in response to an excitation pulse, the displacements measured simultaneously at different locations, wherein measuring the displacements comprises measuring N displacements per receive event for N tracking lines, respectively, and repeating the measuring for the N tracking lines at other times, where N is an integer greater than 8;
    determining a characteristic of a wave generated by the excitation pulse from a comparison of the displacements at the different locations, which displacements were simultaneously measured at the different locations, wherein determining the characteristic comprises locating a peak in the simultaneously measured displacements at the different locations for each of the other times and calculating a velocity as the characteristic from the peaks of the other times; and outputting the characteristic.

19. The non-transitory computer readable storage medium of claim 18 wherein measuring the displacements comprises measuring the displacements in response to the excitation pulse in a pattern of excitation pulses, the displacements measured after transmission of the entire pattern.

* * * * *